United States Patent [19]

Schmidt

[11] 4,140,588
[45] Feb. 20, 1979

[54] PURIFICATION OF PROPYLENE OXIDE BY EXTRACTIVE DISTILLATION

[75] Inventor: John P. Schmidt, Princeton, N.J.

[73] Assignee: Halcon Research and Development Corporation, New York, N.Y.

[21] Appl. No.: 822,289

[22] Filed: Aug. 5, 1977

[51] Int. Cl.² .................... B01D 3/40; C07D 301/02
[52] U.S. Cl. .................................. 203/92; 203/96; 260/348.37
[58] Field of Search .................... 203/95-97, 203/76, 92, 93, 79, 83, 85; 260/348.37

[56] References Cited

U.S. PATENT DOCUMENTS

| | | | |
|---|---|---|---|
| 2,550,847 | 5/1951 | Mitchell et al. | 260/348.37 |
| 2,622,060 | 12/1952 | Robeson et al. | 260/348.37 |
| 2,751,337 | 6/1956 | Goddin et al. | 203/96 |
| 3,409,513 | 11/1968 | Hamlin et al. | 203/96 |
| 3,418,338 | 12/1968 | Gilman et al. | 260/348.37 |
| 3,578,568 | 5/1971 | Washall | 260/348.37 |
| 3,715,284 | 2/1973 | Burns | 260/348.37 |

Primary Examiner—Wilbur L. Bascomb, Jr.
Attorney, Agent, or Firm—William C. Long; David Dick; Riggs T. Stewart

[57] ABSTRACT

Propylene oxide is separated from contaminating quantities of methanol and acetone by extractive distillation with water.

6 Claims, 1 Drawing Figure

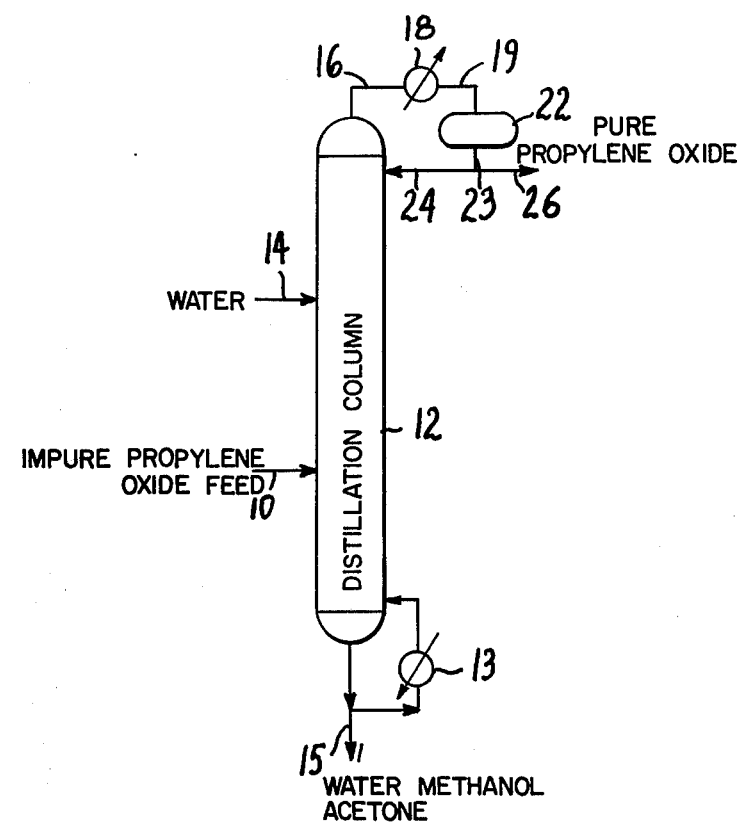

PURIFICATION OF PROPYLENE OXIDE BY EXTRACTIVE DISTILLATION

This invention relates to the purification of propylene and is more particularly concerned with the removal of methanol and acetone from propylene oxide.

Propylene oxide is an important chemical of commerce and is produced in large quantities by the epoxidation of propylene with an organic hydroperoxide, for example as disclosed in Kollar U.S. Pat. No. 3,350,422 of Oct. 31, 1967 and Kollar U.S. Pat. No. 3,351,635 of Nov. 7, 1967, the disclosures of which patents are incorporated herein by reference. The process disclosed in these patents is capable of producing propylene oxide from propylene in high yields using catalysts which comprise at least one metal selected from the group consisting of titanium, vanadium, chromium, selenium, zirconium, niobium, molybdenum, tellurium, tantalum, tungsten, rhenium, and uranium. During the epoxidation reaction, the olefin is epoxidized to form the corresponding oxirane derivative and the organic hydroperoxide is converted to the corresponding alcohol. Following the epoxidation reaction, the liquid reaction product which is withdrawn from the epoxidation zone will comprise, in addition to propylene oxide, unreacted propylene, water, and high-boiling oxygen-containing organic impurities, including the alcohol corresponding to the hydroperoxide employed, such as t-butyl alcohol, alpha-methylbenzyl alcohol, and the like. In addition to such alcohols derived from the hydroperoxide, the impurities generally consist of relatively small amounts of aldehydes such as acetaldehyde, ketones such as acetone, other alcohols such as methanol, hydrocarbons such as hexenes, esters such as methyl formate, and minor quantities of the organic hydroperoxide and/or other peroxidic materials. Depending upon the form of the catalyst employed, the liquid reaction product may or may not contain catalyst components. To recover the product propylene oxide, the reactor effluent is subjected to a series of fractional distillations in order to separate the unreacted propylene, which can be recycled to the epoxidation reactor, and to recover the alcohol, which can be used to form additional quantities of the hydroperoxide for reuse in the oxidation, and in order to separate water and the desired propylene oxide. Distillations of this type are described, for example, in Choo et al. British Pat. No. 1,127,987, in Kaplan U.S. Pat. No. 3,523,956 and in Hoory et al. U.S. Pat. No. 3,632,482, the disclosures of which patents are incorporated herein by reference. It has been found, however, that these fractional distillations are not in themselves sufficient to separate the contaminants which are normally present in relatively small quantities in the propylene oxide and are objectionable for many purposes for which the propylene oxide is conventionally employed. Various processes for purifying propylene oxide with respect to contaminants of this type have been proposed, generally involving extractive distillation with hydrocarbon solvents, for example in Binning et al. U.S. Pat. Nos. 3,337,425 and 3,338,800, in Jubin U.S. Pat. No. 3,464,897 and Schmidt et al. U.S. Pat. No. 3,843,488, and in British Pat. No. 1,059,669 and Belgian Pat. No. 680,816, and the like. Among these objectionable contaminants, however, are methanol and acetone, which may enter the system with the hydroperoxide, particularly in the case of ethyl benzene hydroperoxide, or may come from some other source and, while the processes of the foregoing patents are effective for their intended purposes, it has been found that methanol and acetone, when present, nevertheless resist separation from the propylene oxide and continue to be problem contaminants. Moreover, processes of the type described in the above-mentioned patents require substantial quantities of solvent and necessarily involve a separate distillation step to recover the solvent for reuse, and some of them involve a substantial loss of propylene oxide.

It is, accordingly, an object of the present invention to provide an improved process for the purification of propylene oxide, which involves a single distillation step and wherein contaminating methanol and acetone are effectively removed with minimum loss of propylene oxide.

In accordance with the invention, impure propylene oxide containing contaminating quantitie of methanol and acetone is fractionally distilled in the presence of a controlled small amount of water which serves as an extractive distillation solvent. The amount of water is limited to 2 to 15 weight percent of the impure propylene oxide being treated and in this process, which can be carried out in a single distillation column, purified propylene oxide is directly recovered as an essentially dry overhead distillate substantially free from methanol and acetone, whereas essentially all of the methanol and acetone present in the impure propylene oxide fed to the extractive distillation operation will be found in the aqueous stream withdrawn from the bottom of the column.

Water has heretofore been employed as an extractive distillation solvent for various purposes but, in general, large quantities of water in relation to the feed to the extractive distillation are required or multiple distillations are involved. For example, recently-disclosed processe of this type include MacLean et al. U.S. Pat. No. 3,689,377, Statman et al. U.S. Pat. No. 3,847,756 and Ginnasi et al. U.S. Pat. No. 3,963,586. In U.S. Pat. No. 3,689,377 acrylonitrile is separated from acetonitrile in an operation in which about four parts of water are employed per part of feed and a second distillation is needed to recover all of the product. In U.S. Pat. No. 3,847,756 diethyl ether is recovered from a mixture with ethyl alcohol by extractive distillation with water in an amount ranging from 75 to 300% of the quantity of feed and the product obtained is saturated with water. U.S. Pat. No. 3,963,586 separates dimethyl carbonate from methanol in a process using water as an extractive distillation solvent in an amount corresponding to approximately ten times the amount of feed and the desired dimethyl carbonate is obtained in the presence of a large quantity of water.

Propylene oxide, however, has a substantial solubility in water and is readily hydrolyzed to propylene glycol in the presence of large amounts of water. Thus, processes such as described in the above-mentioned patents, while apparently suitable for their disclosed purposes, cannot be economically applied to the separation of methanol and acetone from propylene oxide.

Bludworth in U.S. Pat. No. 2,198,651 describes a process for the separation of acetone and methanol from a "cyclic ether" which Bludworth characterizes as an unsaturated compound and as including "ethylene oxide, isobutylene oxide, tetramethylene oxide and their homologues and isomers." In this process, which is exemplified with a mixture of methanol, acetone and tetramethylene oxide (tetrahydrofuran), multiple distillations are involved and an extractive distillation with water must be followed by a further distillation in the presence of a hydrocarbon such as butane, pentane, hexane and the like. It is entirely unexpected, therefore, that, in accordance with the present invention, both acetone and methanol can be effectively separated from the propylene oxide in a single fractional distillation operation solely in the presence of water as an extractive distillation solvent with the recovery of the purified propylene oxide as an overhead distillate from the single distillation operation, with minimum loss of the propylene oxide in the feed.

The impure propylene oxide treated in accordance with the process of this invention is typically the product stream resulting from the distillation of an epoxidation reaction mixture, such as produced by the processes described in the above-mentioned Kollar, Choo et al. and Kaplan patents, wherein the product stream is separated from unreacted propylene, solvent such as ethyl benzene, the alcohol derived from the hydroperoxide employed in the epoxidation, e.g. alpha phenyl ethanol, water, catalyst, if present, and the like. Typical of processes for separating propylene oxide from such components of the epoxidation reaction mixture are those described in Choo et al. British Pat. No. 1,127,987 and Kaplan U.S. Pat. No. 3,523,956, referred to above. Other separation processes can, however, be used, as will be readily apparent to persons skilled in this art. The process of the invention is particularly applicable to impure propylene oxide produced by the epoxidation of propylene with an alkaryl hydroperoxide, particularly ethyl benzene hydroperoxide. Preferably this propylene oxide product stream has also been previously treated to remove all or substantially all of the contaminants other than methanol and acetone which may originally have been present in it, such as acetaldehyde, methyl formate, hydrocarbons such as hexenes, and the like, for example, by the methods described in the Jubin and Schmidt U.S. patents and in the British and Belgian patents referred to above. In other words, the impure propylene oxide is preferably one which contains essentially only methanol and acetone as contaminants in amounts which are objectionable and require removal to produce a propylene oxide of commercially attractive purity. It is, however, within the scope of this invention to apply the extractive distillation with water to an impure proplylene oxide which has not previously been treated to remove other minor contaminants and it has been found that the extractive distillation process of this invention will effectively substantially completely separate methanol and acetone even when other contaminants are present. Thus, the impure propylene oxide feed to the extractive distillation will be predominantly propylene oxide but may, in addition to the acetone and methanol to be removed, contain varying amounts of other components contained in the effluent from the epoxidation reaction, principally aldehydes such as acetaldehyde and propionaldehyde, hydrocarbons such as hexenes, and small amounts of water. Thus, a typical impure propylene oxide feed will comprise:

|  | % by Weight |
| --- | --- |
| Propylene oxide | 92 to 99 |
| Water | 0.3 to 5.0 |
| Methanol | 0.01 to 0.30 |
| Acetone | 0.01 to 0.30 |
| Other Impurities | 0.01 to 2.0 |

-continued

|  | % by Weight |
| --- | --- |
| (Aldehydes, hexenes, etc.) |  |

Any water present in the feed is taken into consideration in the calculation of the amount of water to be supplied to the extractive distillation. Thus, if the feed already contains 1% water, and it is desired to effect the extractive distillation with 8% water, based on the weight of the feed, then only the additional 7% of water is introduced into the column as an extractive distillation solvent. Whatever the content of water in the feed, however, the amount of water supplied as a separate extractive distillation solvent stream is at least about 1%, based on the weight of the feed.

The extractive distillation is suitably carried out in any convenient fractional distillation zone appropriate for the distillation of propylene oxide. For best results, the fractional distillation zone should contain at least 15 theoretical plates, and ordinarily will contain 20 to 40 theoretical plates. The maximum number of theoretical plates is limited only by economic considerations.

For economic reasons the fractional distillation zone should generally comprise a single distillation column, although the use of multiple distillation columns to accomplish the same result is not excluded.

It has been found that the distillation must be carried out under carefully controlled conditions in order to remove the acetone and methanol without excessive loss of propylene oxide. First, the amount of water supplied should be between 2 and 15 weight percent of the propylene oxide feed stream. Second, the feed point for the water should be between the propylene oxide feed point and a point not higher than eight theoretical plates above the propylene oxide feed point.

The location of the propylene oxide feed point itself is less critical than the above-mentioned factors but it should be in the lower portion of the distillation zone, and preferably from about one fifth to about two fifths of the distance, in terms of theoretical trays, from the bottom to the top of the distillation zone.

A suitable reflux/propylene oxide feed ratio is important in bringing about optimum results and this reflux ratio should range between 3:1 and 12:1. The pressure under which the extractive distillation is conducted is suitably atmospheric pressure or moderate super-atmospheric pressure, e.g. up to about 30 lbs. per square inch absolute. The bottoms temperature will, of course, vary with the pressure, but will generally lie within the range of 60° to 100° C.

When the extractive distillation is suitably carried out under the abovementioned conditions, the bottoms from the distillation zone should contain at least 80% of the methanol and 80% of the acetone, and not more than 3% of the propylene oxide, including loss as glycol, contained in the feed stream to the distillation.

In the accompanying drawing there is illustrated diagrammatically a representative system for carrying out the extractive distillation process of this invention. Thus, referring to the drawing, the reference numeral 10 designates the line for feeding the impure propylene oxide to be treated to a fractional distillation column 12, to which heat is supplied by means of a reboiler 13. Water is supplied as the extractive distillation solvent through line 14. The aqueous bottom stream containing essentially all of the water, methanol and acetone introduced into the column is withdrawn through line 15 and the overhead vapors consisting essentially only of the purified propylene oxide are removed via line 16 and are condensed in condenser 18, the condensate then passing through line 19 to reflux drum 22 where the condensate is accumulated. From line 23 the appropriate quantity of the distillate is returned to the column via line 24 as reflux, and the remainder is withdrawn through line 26.

The following examples will serve to provide a fuller understanding of the invention, but it is to be understood that these examples are given by way of illustration only and are not to be interpreted a limiting the invention.

EXAMPLE I

A crude propylene oxide recovered from an epoxidation effluent in which propylene is epoxidized with ethyl benzene hydroperoxide in the presence of a molybdenum catalyst and the effluent is distilled to remove unreacted propylene, ethyl benzene, acetophenone, alpha phenyl ethanol and low-boiling components such as acetaldehyde has the following composition:

|  | % by weight |
|---|---|
| acetaldehyde | trace |
| propionaldehyde | 0.04 |
| acetone | 0.16 |
| hexenes | 0.05 |
| water | 1.5 |
| methanol | 0.06 |
| propylene oxide | balance |

This impure propylene oxide is continuously fed at the rate of 100 parts by weight per hour to the 14th tray from the bottom of a fractional distillation column containing 60 actual trays. The column is operated at 20 psia with a bottoms temperature of about 70° C. and a reflux/feed ratio of 9. At the same time, water is supplied to the 20th tray from the bottom of the fractionating column (about 4 theoretical trays above the propylene oxide feed tray) at a rate of 6 parts by weight per hour, making a total water feed of 7.5 parts per hour. The condensed overhead distillate is found to be substantially pure propylene oxide containing only 29 ppm methanol, less than 100 ppm water and merely a trace of acetone. The bottoms stream is found to contain more than 95% of the methanol and more than 98% of the acetone in the feed and its content of propylene oxide plus propylene glycol formed by hydrolysis is only 1.3% of the propylene oxide fed to the distillation.

EXAMPLE II

Example I is repeated, but with lesser and greater water feed rates, with the following results:

| Total Water Feed (parts by weight) | % Methanol Removal | % PO Losses |
|---|---|---|
| 3.0 | 86 | 0.7 |
| 9.5 | 97 | 1.7 |
| 14.0 | 98 | 2.5 |

In each case acetone removal is greater than 90%.

COMPARATIVE EXAMPLE A

Example I is repeated, except that water is introduced upon the 30th tray from the bottom (about 10 theoretical trays above the propylene oxide feed tray). Methanol and acetone removal are greater than 98% but the loss of propylene oxide, including loss as glycol, is more than 3%.

COMPARATIVE EXAMPLE B

Example I is again repeated, except that water is introduced upon the 8th tray from the bottom. Methanol removal is less than 80%.

COMPARATIVE EXAMPLE C

Example I is repeated, except that water is introduced at the rate of 75 parts per weight per 100 parts of propylene oxide feed. Methanol and acetone removal are greater than 98% but the loss of propylene oxide, including loss as glycol, is more than 10%.

COMPARATIVE EXAMPLE D

Example I is repeated, except that no water is fed to the distillation column beyond that contained in the propylene oxide feed. Methanol removal is less than 40%.

What is claimed is:

1. An extractive distillation process effective for the separation of methanol and acetone from propylene oxide in a single distillation zone, which comprises introducing the feed comprising propylene oxide contaminated with methanol and acetone into a fractional distillation zone containing at least 15 theoretical plates, said propylene oxide feed being introduced into a lower portion of said zone, introducing an extractive distillation agent consisting essentially of water into said zone at a point between the point of introduction of the propylene oxide feed and a point not higher than eight theoretical plates above the propylene oxide feed point, said water being introduced in an amount representing between 2 to 15% by weight of the propylene oxide feed, distilling said propylene oxide feed in the presence of said water at a pressure between about atmospheric and 30 lbs. per square inch absolute, recovering propylene oxide purified with respect to said methanol and acetone as an overhead distillate from said distillation zone, and withdrawing from said distillation zone an aqueous bottoms stream containing substantially all of the water and the methanol and acetone introduced into said distillation zone.

2. A process as defined in claim 1, wherein said distillation is carried out with a reflux to propylene oxide feed ratio of 3:1 to 12:1.

3. A process as defined in claim 1, wherein the amount of water introduced into said distillation zone is 3 to 10 weight percent of the propylene oxide feed.

4. A process as defined in claim 1, wherein the propylene oxide feed is introduced at a point between about one fifth to about two fifths of the distance, in terms of theoretical trays, from the bottom to the top of the distillation zone.

5. A process a defined in claim 1, wherein at least 80% of the methanol and 80% of the acetone contained in the feed are withdrawn in the bottoms from the distillation zone.

6. A process as defined in claim 1, wherein the bottoms from the distillation zone contain not more than 3%, including loss as propylene glycol, of the propylene oxide fed to the distillation.

* * * * *